US006517237B1

(12) United States Patent
Hammond et al.

(10) Patent No.: US 6,517,237 B1
(45) Date of Patent: *Feb. 11, 2003

(54) MEASURING ENERGY CONSUMPTION

(75) Inventors: Paul Steven Hammond, Ashby de la Zouch (GB); Robert Richard Thurston, Melbourne (GB); Barry Leonard Price, Quorn (GB)

(73) Assignee: Lattice Intellectual Property Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/784,441

(22) PCT Filed: Aug. 20, 1999

(86) PCT No.: PCT/GB99/02714

§ 371 (c)(1),
(2), (4) Date: Feb. 23, 2001

(87) PCT Pub. No.: WO00/11465

PCT Pub. Date: Mar. 2, 2000

(30) Foreign Application Priority Data

Aug. 25, 1998 (GB) ............................................. 9818388

(51) Int. Cl.$^7$ ............................................. G01K 17/00
(52) U.S. Cl. ........................... 374/31; 374/36; 73/24.01
(58) Field of Search ........................... 374/31, 35, 36; 73/24.01, 23.31, 24.06, 31.05

(56) References Cited

U.S. PATENT DOCUMENTS 4,246,773 A   1/1981  Haruta
5,528,924 A * 6/1996  Wajid et al. ................ 73/24.01
5,537,854 A * 7/1996  Phillips et al. ............. 73/24.01
5,635,626 A * 6/1997  Hammond et al. .......... 73/23.2
5,697,346 A * 12/1997 Beck .......................... 73/23.31

FOREIGN PATENT DOCUMENTS

| GB | 2 210 977 | 6/1989 |
| GB | 2 312 508 | 10/1997 |
| WO | WO 99/36767 | 7/1999 |

* cited by examiner

*Primary Examiner*—Diego Gutierrez
*Assistant Examiner*—Mirellys Jagan
(74) *Attorney, Agent, or Firm*—Oblon, Spivak, McClelland, Maier & Neustadt, P.C.

(57) ABSTRACT

An energy meter which measures a volume of gas supplied, which measures a calorific value of the gas supplied, and which calculates an energy value corresponding to the measured volume of gas supplied and the calorific value. The structure to measure the volume of the gas supplied and to calculate the energy value may be provided in a single unit. The structure to measure the calorific value of the gas supplied preferably includes a structure to measure the speed of sound in the gas and further preferably measures a first thermal conductivity of the gas at a first temperature and measures a second thermal conductivity of the gas at a second temperature which differs from the first temperature, and is arranged to produce the calorific value of the gas corresponding to the measured speed of sound in the first and second thermal conductivities.

22 Claims, 2 Drawing Sheets

MEASURING ENERGY CONSUMPTION

BACKGROUND OF THE INVENTION

1. Field of the Invention

This invention relates to an energy meter and a method of metering consumed energy. This invention is particularly applicable to the supply of energy in the form of fuel gas.

2. Discussion of the Background

Conventionally energy consumption in the form of fuel gas is determined for billing purposes by measuring the volume of gas supplied to the consumer by providing a gas flow meter at the point of delivery. The gas supplier also remotely monitors the quality of gas supplied to a distribution area occupied by the consumer using the calorific value (CV) of the gas which is the fundamental measure of energy per unit volume, generally measured with a large and expensive chromatograph. From the CV of the gas supplied to the area together with the reading of the volume of fuel gas consumed by the customer, the gas supplier is able to determine the energy consumption from which the consumer is charged.

SUMMARY OF THE INVENTION

As the customer is only able to determine the volume, of gas consumed without knowing the gas quality, he is unable to precisely monitor how much he will be charged. This is particularly disadvantageous for pre-payment "coin operated" gas meters.

According to a first aspect of the present invention an energy meter comprises:

means to measure a volume of gas supplied;

means to measure a calorific value of the gas supplied; and means to calculate an energy value corresponding to the measured volume of gas supplied and the measured calorific value wherein both of the means to measure a volume of gas supplied and the means to measure a calorific value of the gas supplied are provided in a single integral meter unit.

According to a second aspect of the present invention a method of determining a quantity of energy supplied to a consumer comprises:

measuring a volume of gas supplied;

measuring a calorific value of the gas supplied; and calculating an energy value of the supplied gas corresponding to the measured volume of gas supplied and the measured calorific value wherein both the measuring of a volume of gas supplied and the measuring of a calorific value of the gas supplied are performed at substantially the point of delivery to the consumer.

The provision of an energy reading at the customer,s premises enables the consumer to monitor how much he will be charged. This is especially advantageous for pre-payment meters.

According to a further aspect of the present invention an energy meter comprises:

means to measure a volume of gas supplied;

an apparatus to measure a calorific value of the gas including means to measure the speed of sound in the gas and means to use the speed of sound in an operation producing the calorific value of the gas corresponding to said speed of sound; and means to calculate an energy value corresponding to the measured volume of gas supplied and the measured calorific value.

According to a still further aspect of the present invention a method of determining a quantity of energy supplied comprises:

measuring a volume of gas supplied;

measuring a calorific value of the gas supplied including measuring the speed of sound in the gas and using the speed of sound in an operation producing the calorific value of the gas corresponding to said speed of sound; and calculating an energy value of the supplied gas corresponding to the measured volume of gas supplied and the measured calorific value.

The means to measure a volume of gas supplied and the apparatus to measure the calorific value of the gas are preferably provided in a single unit. The means to calculate an energy value may also be provided in the same unit but may additionally or alternatively be provided remotely, for example at the gas supplier's billing department.

Since the speed of sound of a gas can be determined by a conveniently compact and inexpensive device it can be provided in a small meter unit and provided with correspondingly compact means, preferably in the form of control electronics or a processing means, to produce the calorific value from the measured speed of sound. Such an apparatus to measure a calorific value of the gas is much smaller, cheaper and easier to operate than a conventional calorific value measuring device such as a chromatograph. Consequently, this enables the production of a meter to measure energy which is small, cheap and reliable when used with a means to measure a volume of gas supplied.

The calorific value of a gas is preferably measured by making a measure of a first thermal conductivity of the gas at a first temperature, making a measure of a second thermal conductivity of the gas at a second temperature which differs from the first temperature, and using the speed of sound and the first and second thermal conductivities in an operation producing the calorific value of the gas corresponding to said speed of sound and said first and second thermal conductivities.

The above described meter and method are suitable for both domestic and industrial use.

All references to the calorific value include parameters equivalent to calorific value such as Wobbe Index $x\sqrt{RD}$. All references to calorific value also include parameters dependent upon calorific value which when considered with the volume of gas supplied produce a parameter dependent upon the energy value.

All references to energy value include parameters dependent upon energy values such as cost in the local currency. The cost is determined by multiplying the consumed energy, measured in Joules or Watt hours for example, by the cost per unit of energy.

BRIEF DESCRIPTION OF THE DRAWINGS

The invention will now be further described, by way of example, with reference to the accompanying drawings in which.

DESCRIPTION OF THF PREFERRED EMBODIMENTS

Figure 1:
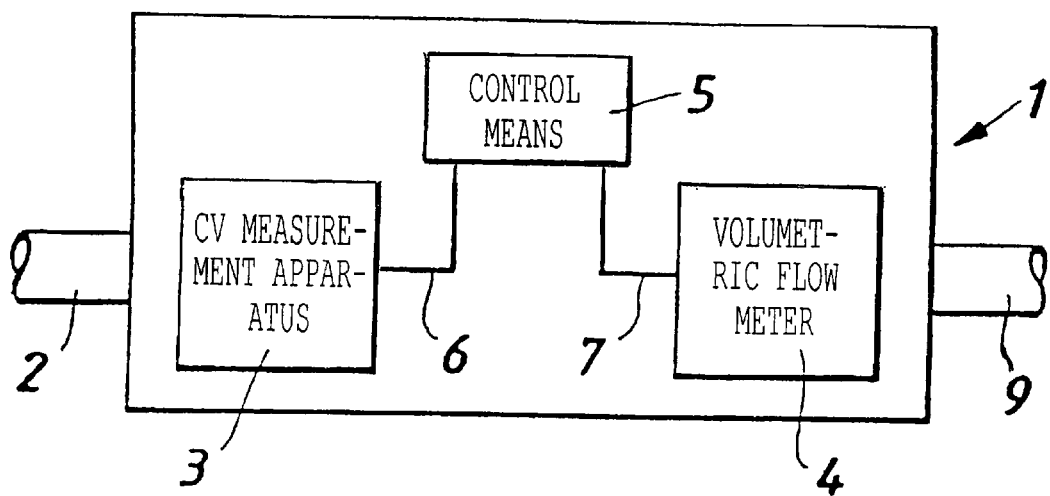
FIG. 1 diagrammatically shows an apparatus in which the invention can be performed.

With reference to FIG. 1 an energy meter 1 is arranged to receive a supply of fuel gas from an inlet 2 and to supply fuel gas to a user via an outlet 9. The meter 1 comprises a calorific value (CV) measurement apparatus 3, a volumetric flow meter 4 to measure a volume of gas supplied and control means 5 connected to the CV measurement apparatus 3 via connection 6 and to flow meter 4 via connection 7 to calculate an energy value of the supplied gas from the CV and the volume of gas supplied. In the example shown in FIG. 1 fuel gas is supplied to the CV measurement apparatus 3 by the inlet 2 and supplied to the volumetric flow meter 4 from the CV measurement apparatus 3 by conduit and is arranged to leave volumetric flow meter 4 via the outlet 9 to be consumed by a user.

The CV measurement apparatus 3 may comprise any means to measure the speed of sound of the gas and a means to use the speed of sound in an operation producing the calorific value of the gas corresponding to the measured speed of sound.

Figure 2:
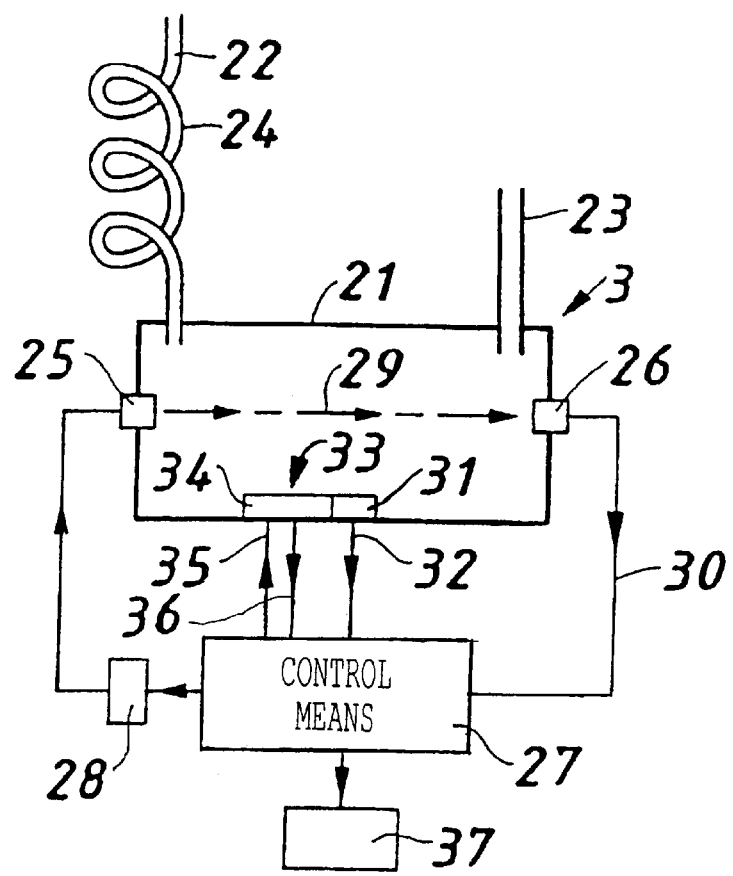
FIG. 2 diagrammatically shows an apparatus for measuring the calorific value of a gas.

With reference to FIG. 2, the illustrated apparatus 3 to measure the calorific value of a gas has a chamber 21 into which the gas is supplied through an inlet conduit 22 and leaves through an outlet conduit 23. The inlet conduit 22 includes heat exchange means 24 for example a copper coil by which the temperature of the incoming gas can be adjusted to a value substantially the same as that of the ambient temperature of the external atmosphere whereby the gas in the chamber 21 is of substantially uniform temperature throughout. The chamber 21 includes an ultra-sound emitter transducer 25 and an ultra sound receiver transducer 26. An electronic control means 27 including computer means is connected to a signal generator 28 so that under the control of the control means 27 the signal, generator causes the transducer 25 to emit ultra-sound signals 29 as desired. The ultra-sound signals 29 are received by the transducer 26 and their reception signalled to the control means 27 via line 30. The time of flight of the ultra-sonic signals between transducers 25 and 26 is measured by the control means 27 which is arranged to calculate SoS which is the speed of sound in metres/second (m/s).

Any means for measuring the speed of sound in the gas may be used, such as that disclosed in U.S. Pat. No. 4,938,066. However, the most preferable method is that disclosed in UK patent application Nos GB 9813509.8, GB 9813513.0 and GB 91813514.8. These applications disclose the use of an acoustic resonator to measure the speed of sound of a gas within the resonator. A driving electronic circuit which may include or be in the form of a microprocessor is arranged to produce a sinusoidal signal over a suitable range of frequencies to drive a loudspeaker. The loudspeaker is arranged to apply an acoustic signal to the interior of a resonator. A microphone is arranged to detect the magnitude of the acoustic signal within the resonator. The signal from the microphone is filtered and amplified by an appropriate electronic circuit and a processing means determines the resonant frequency relating to the gas within the resonator and from this is able to determine the speed of sound of the gas.

A temperature sensor 31 in the chamber 21 provides the control means 27 with data on line 32 representing the value of the ambient temperature.

The ambient temperature sensor 31 may be part of a thermal conductivity. sensor 33 comprising thermal conductivity observation means 34. The thermal conductivity sensor 33 may be a miniature thermal conductivity microsensor model type TCS208 available from Hartmann B Braun AG of Frankfurt am Main, Germany, but any suitable thermal conductivity sensor will suffice.

The thermal conductivity observation means 34 to observe the thermal conductivity of the gas has heater means which in response to signals on line 35 from the control means 27 can operate at more than one selected desired temperature above the ambient temperature observed by the sensor 31, and a signal representative of the, thermal conductivity of the gas at the desired temperature is sent to the control means on line 36.

The control means 27 is arranged to cause the thermal conductivity sensor 33 to measure the thermal conductivity of the gas at two different desired temperatures $t_H$ and $t_L$ in which $t_H$ is a pre-determined desired number of temperature degrees $t_1$ above the ambient temperature observed by the sensor 31 and $t_L$ is a predetermined desired number of temperature degrees $t_2$ above ambient temperature; the number $t_1$ being greater than the number $t_2$.

Using the observed or measured values of the speed of sound in the gas, the thermal conductivity of the gas at temperature $t_H$ and $t_L$ and the observed value of the ambient temperature of the gas by sensor 31, the control means 27 calculates the calorific value of the gas using the formula $$CV = a \cdot ThC_H + b \cdot ThC_L + c \cdot SoS + d \cdot T_a + e \cdot T_a^2 + f, \qquad \text{(Equation I)}$$

in which

CV is the calorific value;

$ThC_H$ is the thermal conductivity of the gas at temperature $t_H$;

$ThC_L$ is the thermal conductivity of the gas at temperature $t_L$;

SoS is the speed of sound in the gas at the ambient temperature;

$T_3$ is the ambient temperature of the gas observed by the sensor 31, and a, b, c, d, e and f are respective constants.

The gas in question may be a mixture of two or more gases in which the composition of the mixture may be of variable proportions. For example the gas in question may be a fuel gas. Such a fuel gas may be natural gas. The natural gas may comprise methane and at least one of ethane, propane, butane, pentane or hexane, and may further comprise nitrogen and/or carbon dioxide.

In order to derive the constants a, b, c, d, e, and f in equation I, the mathematical technique known as regression analysis may be used in respect of data collected in connection with the gas in question. The proportions of gases in the mixture may be varied to form a number of different samples. Using chromatographic methods the calorific value (CV) of a sample is obtained, the ambient temperature $T_a$ of the sample is measured and the thermal activities $ThC_H$ and $ThC_L$ of the sample are measured. This is done for each sample in turn to obtain a set of measured values corresponding to each sample. The sets of values are inserted in equation I and the "best-fit" values for constants a, b, c, d, e and f are derived. In the case of natural gas coming ashore at a number of locations in the United Kingdom regression analysis was performed on samples from the different locations and also on gas equivalence groups which are artificial replications in the laboratory of mixtures of methane and ethane, methane and butane, methane and pentane, and methane and hexane in which, in the laboratory, those mixtures are represented by different mixtures of methane and propane.

When equation I was applied to natural gas and to gas equivalence groups and regression analysis used, the following values for the constants were derived, namely:

a=36.25649,
b=−45.5768,
c=0.047029
d=0.091067,
e=0.00074, and
f=24.18731, when
  CV is the calorific value of gas in MJ/m³,(Megajoules/ standard cubic metres);
  $ThC_H$ is the thermal conductivity of the gas in W/m·K (where K is degrees Kelvin) at a temperature of substantially 70 degrees Celsius above ambient temperature $T_a$;
  $ThC_L$ is the thermal conductivity of the gas in W/m·K at a temperature $t_L$ which is substantially 50 degrees Celsius above ambient temperature $T_a$;
  SoS is the speed of sound in the gas in m/s, and $T_a$ is the ambient temperature of the gas in degrees Celsius.

In the above application of equation I to natural gas the value of $t_1$ is substantially 70° C. and the value of $t_2$ is substantially 50° C. Thus the difference between the temperatures $t_H$ and $t_L$ at which the thermal conductivities $ThC_H$ and $ThC_L$ are measured differ by substantially 20° C. [$(T_a+70)-(T_a+50)=20$]. However, constants may be determined for any suitable temperatures at which the thermal conductivities $ThC_H$ and $ThC_L$ are measured.

The value of the calorific value CV of the gas calculated by the control means 27 may be visually displayed and/or printed or otherwise recorded by recording means 37 in response to signals from the control means.

By any suitable technique know per se the control means 27 may be provided with information representing the relative density of the gas or the control means may be provided with information enabling it to calculate the relative density (RD) of the gas. The control means 27 may calculate or otherwise obtain the value of the Wobbe Index WI of the gas using the formula $$WI = \frac{CV}{\sqrt{RD}}$$

A method of measuring relative density is described in our UK patent application No. GB9715448.8 filed on Jul. 22nd 1997.

The volume of fuel gas consumed may be determined by any suitable volumetric flow meter 4.

Figure 3:
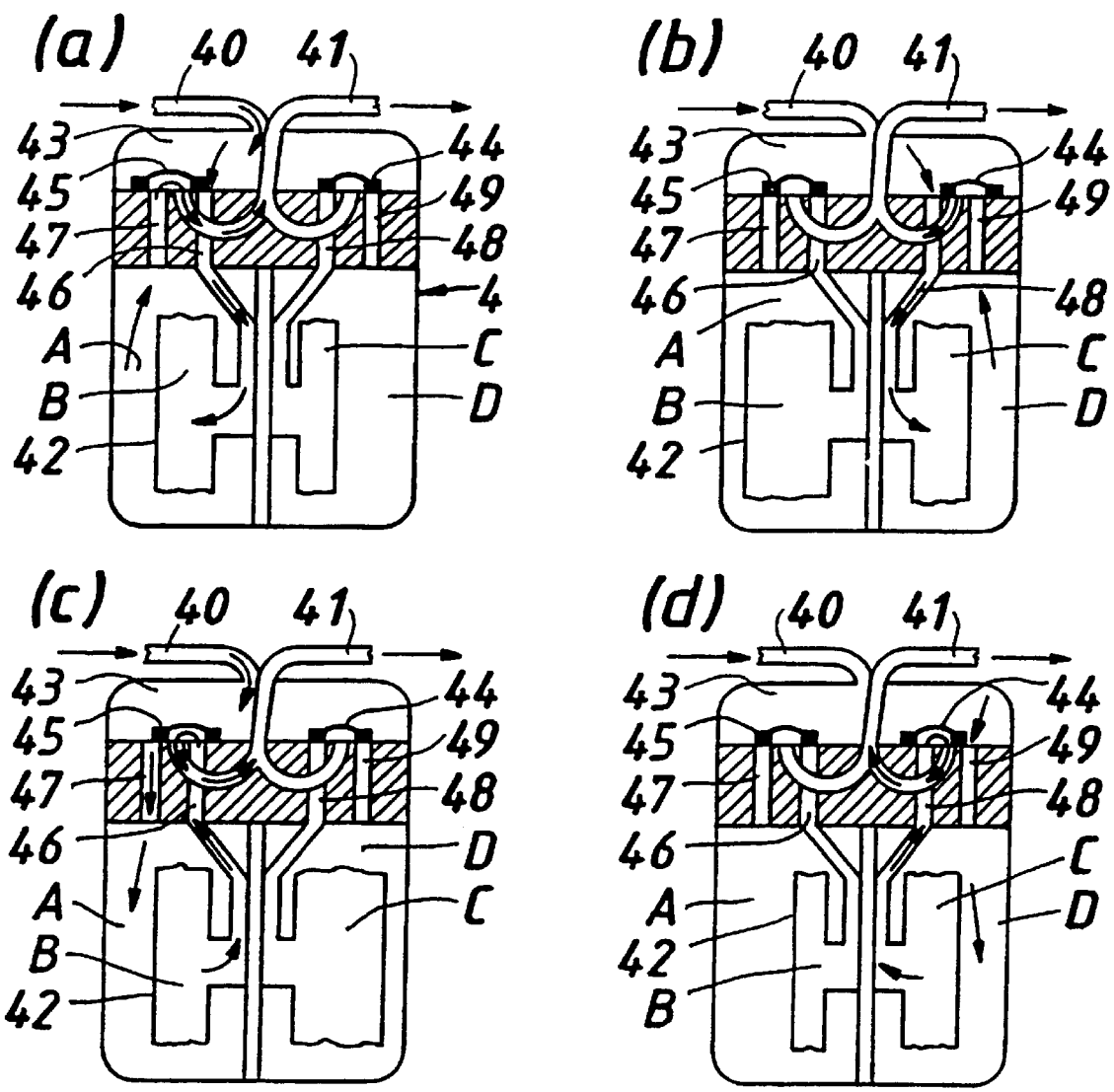
FIG. 3 diagrammatically shows an apparatus for measuring a volume of gas consumed.

For example a diaphragm meter as shown in FIG. 3 may be used which is particularily suitable for use with domestic low pressure supplies. The illustrated meter has an inlet 40, an outlet 41 and four interconnected chambers A, B, C, D, two of which B, C are enclosed by bellows 42. The porting of the chambers is controlled by interconnected slide valves 44, 45.

As shown in FIG. 3(a) with the interconnected valves 44, 45 in a first position, fuel gas from the inlet 40 enters an upper chamber 43 and passes through conduit 46 into chamber B which expands. As chamber B expands, chamber A is correspondingly contracted so that it expels fuel gas to the outlet 41 through conduit 47 and slide valve 45. Meanwhile conduits 48, 49 to chambers C, D respectively are blocked by slide valve 44. As chamber B of the bellows 42 expands it moves the interconnected slide valves 44, 45 either directly or indirectly via a mechanical linkage for example, to the position shown in FIG. 3(b).

In this position conduits 46 and 47 are blocked by slide valve 45 and fuel gas passes from upper chamber 43 through conduit 48 into chamber C which expands. As chamber C expands, chamber D is correspondingly contracted so that it expels fuel gas to the outlet 41 through conduit 49 and slide valve 44. As chamber C expands interconnected slide valve 44, 45 is moved to the position shown in FIG. 3(c) in which conduits 48, 49 are blocked by slide valve 44.

In this position fuel gas from upper chamber 43 passes through conduit 47 to chamber A which expands. As chamber A expands, chamber B is correspondingly contracted so that it expels fuel gas to the outlet 41 via conduit 46 and slide valve 45. As chamber B contracts the interconnected slide valves 44, 45 move to the position shown in FIG. 3(d).

In this position conduits 46, 47 are blocked and fuel gas passes from upper chamber 43 to chamber D through conduit 49. As chamber D expands, chamber C is correspondingly contracted so that it expels fuel gas to the outlet 41 via conduit 48 and slide valve 44. As chamber D expands the interconnected slide valves 44, 45 are moved to the position shown in FIG. 3(a) and the process is repeated.

The rate of movement of the slide valve mechanism 44, 45 is indicative of the rate of flow of gas and so is indicative of the volume of gas consumed. The slide valve mechanism is connected to a counter which records the number of cycles performed by the valve mechanism 44, 45 and so determines the rate of consumption and the volume of gas consumed. The counter is preferably electronic and sends an electrical signal corresponding to the volume of gas consumed to the control means 5.

Another commonly used meter suitable for determining the volume of gas consumed in the present invention is an ultrasonic meter as disclosed in our UK patent No. GB 2259571.

Any other suitable method of determining the volume of gas consumed may be used such as an orifice plate, a venturi meter, a rotary gas meter, a turbine meter etc. as are well known in the art and as may be suitable for the particular circumstances such as industrial use, domestic use etc. Domestic supplies would generally use a diaphragm meter as disclosed with reference to FIG. 3. Relatively low volume industrial users would generally use a large version of the diaphragm meter, larger industrial users (95 m³/hour) may use a rotary meter and even larger users (250 m³/hour) may use a turbine meter.

The control means 5 which may be a processing means such as a microprocessor or a computer or a suitable electronic circuit is arranged to receive signals indicative of the rate of supply or volume of fuel gas consumed together with signals indicative of the CV of the gas being supplied. The control means 5 may be incorporated in or associated with the control means 27 of the apparatus for measuring the CV of the gas 3 or the control means 5, 27 may be separate from each other. The control means, 5 may be provided remote from CV measurement apparatus 3 and volumetric flow meter 4 such as at the supplier's billing department.

The control means 5 may be connected to a display means and/or a recording means either or both of which may be in, on, or close to the meter and/or remote from it such as at the gas distributing company's billing department.

The control means 5 is arranged to determine the energy supplied using the equation $$\text{Energy supplied} = kAB$$

where k is a constant, A is the volume of gas supplied in a particular period of time and B is the average calorific value during this period.

The particular period of time may be any period suitable depending upon the rate of change of A and B.

If A is measured in units of m³ and B is measured in units of MJ/m³, the energy supplied is measured in units of MJ. k is dimensionless and is a volume correction factor to bring the volumetric reading to metric standard conditions (MSC) of 15° C. and 1013.25 mbar and is dependent upon the ambient temperature and pressure which may be affected by the altitude.

k is calculated using the expression:

$$k = \frac{P_{actual}}{P_{corrected}} \times \frac{T_{corrected}}{T_{actual}}$$

where P is pressure in mbar and T is temperature in Kelvin, where $$\frac{P_{actual}}{P_{corrected}} = \frac{(1013.25 + \text{meter supply pressure} - \text{attitude correction})}{1013.25}$$

and $$\frac{T_{corrected}}{T_{actual}} = \frac{288.15}{(\text{Average Temperature} + 273.15)}$$

If, for example, the meter supply pressure was 21 mbarg and the altitude correction was 7.99 mbar (for an assumed altitude of 66 m and a temperature of 12.2° C.) $P_{actual}/P_{corrected}$ would be 1.01284 and if the average temperature is 12.2° C., $P_{corrected}/P_{actual}$ would be 1.00981. k would then be 1.01284×1.00981 =1.02278.

Although the invention has been described with reference to a particular example, many modifications are within the scope of the invention claimed. For example any method or apparatus for measuring the speed of sound may be used and any method or apparatus may be used to measure the volume of gas supplied.

What is claimed is:

1. An energy meter for measuring a quantity of energy supplied in the form of gas comprising:
    means to measure a volume of gas supplied;
    an apparatus to measure a calorific value of the supplied gas including means to measure the speed of sound in the gas and means to use the speed of sound in an operation producing the calorific value of the gas corresponding to said speed of sound; and
    means to calculate an energy value corresponding to the measured volume of gas supplied and the measured calorific value;
    wherein the apparatus to measure the calorific value of the gas further includes means to measure a first thermal conductivity of the gas at a first temperature, and means to measure a second thermal conductivity of the gas at a second temperature which differs from the first temperature, and
    wherein the means producing the calorific value of the gas uses the first and second thermal conductivities in addition to the speed of sound in the operation producing the calorific value of the gas corresponding to the speed of sound and the first and second thermal conductivities.

2. An energy meter according to claim 1, in which the first temperature is substantially 70° C. above ambient temperature.

3. An energy meter according to claim 1, in which the second temperature is substantially 50° C. above the ambient temperature.

4. An energy meter according to claim 1, wherein the means to measure the speed of sound in the gas is a resonator arranged to contain samples of the gas supplied, the resonator being arranged to have an acoustic signal over a range of frequencies applied to its interior when it contains samples of the gas supplied and having means to detect the magnitude of the acoustic signal within the resonator at each applied frequency and from the resonant frequency determine the speed of sound of the gas.

5. An energy meter according to claim 1, wherein the means to measure a volume of gas supplied is a gas flow meter.

6. An energy meter according to claim 5, wherein the gas flow meter is a diaphragm meter.

7. An energy meter according to claim 5, wherein the gas flow meter is an ultrasonic meter.

8. An energy meter according to claim 1, including means to measure the ambient temperature of the gas and wherein the means producing the calorific value of the gas is arranged to use the formula:

$$CV = a \cdot ThC_H + b \cdot ThC_L + c \cdot SoS + d \cdot T_a + e \cdot T_a^2 + f,$$

where CV is the calorific value of the gas,
where $ThC_H$ is the first thermal conductivity of the gas at said first temperature,
where $THC_L$ is the second thermal conductivity of the gas at said second temperature which is lower than said first temperature,
where SoS is the speed of sound in gas at ambient temperature, and
where $T_a$ is the ambient temperature of said gas whereof said thermal conductivities are measured, the first and second temperatures being greater than said ambient temperature, and a, b, c, d, e, and f are constants.

9. An energy meter according to claim 8, in which SoS is the speed of sound in m/s, the thermal conductivities are in units of Watts/meter×degrees Kelvin (W/m·k), the temperature $T_a$ and the first and second temperatures are in degrees Celsius, and the calorific value is in megajoules/standard cubic metre ($MJ/m^3_{st}$).

10. An energy meter according to claim 8, in which the meter is arranged to measure the energy value of fuel gas.

11. An energy meter according to claim 10, in which the fuel gas is natural gas.

12. An energy meter according to claim 11, in which the gas comprises at least one hydrocarbon gas which is methane, and at least one of nitrogen and carbon dioxide.

13. An energy meter according to claim 11, in which:
    a is substantially 36.25649,
    b is substantially −45.5768,
    c is substantially 0.047029,
    d is substantially 0.091067,
    e is substantially 0.00074, and
    f is substantially 24.18731.

14. A method of measuring a quantity of energy comprising:
    measuring a volume of gas supplied;
    measuring a calorific value of the supplied gas including measuring the speed of sound in the gas and using the speed of sound in an operation producing the calorific value of the gas corresponding to said speed of sound; and
    calculating an energy value corresponding to the measured volume of gas supplied and the measured calorific value;
    wherein the measurement of the calorific value of the gas further includes measuring a first thermal conductivity of the gas at a first temperature, measuring a second thermal conductivity of the gas at a second temperature which differs from the first temperature, and producing the calorific value of the gas using the first and second thermal conductivities in addition to the speed of sound in the operation producing calorific value of the gas corresponding to the speed of sound, and the first and second thermal conductivities.

15. A method according to claim 14, in which the first temperature is substantially 70° C. above ambient temperatures.

16. A method according to claim 14, in which the second temperature is substantially 50° C. above the ambient temperature.

17. A method according to claim 14, including measuring the ambient temperature of the gas and producing the calorific value of the gas using the formula:

$$CV = a \cdot ThC_H + b \cdot ThC_L + c \cdot SoS + d \cdot T_a + e \cdot T_a^2 + f,$$

where CV is the calorific value of the gas, where $ThC_H$ is the first thermal conductivity of the gas at said first temperature, where $THC_L$ is the second thermal conductivity of the gas at said second temperature which is lower than said first temperature, where SoS is the speed of sound in gas at ambient temperature and where $T_a$ is the ambient temperature of said gas whereof said thermal conductivities are measured, the first and second temperatures being greater than said ambient temperature, ad a, b, c, d, e and f are constants.

18. A method according to claim 17, in which SoS is the speed of sound in m/s, the thermal conductivities are in units of Watts/meter×degrees Kelvin (W/m·k), the temperature $T_a$ and the first and second temperatures are in degrees Celsius, and the calorific value is in megajoules/standard cubic metre ($MJ/m^3_{st}$).

19. A method according to claim 17, wherein the quantity of energy measured is the energy value of a fuel gas.

20. A method according to claim 19, in which the fuel gas is natural gas.

21. A method according to claim 20, in which the gas comprises at least one hydrocarbon gas which is methane, and at least one of nitrogen and carbon dioxide.

22. A method according to claim 20, in which:

a is substantially 36.25649, b is substantially −45.5768, c is substantially 0.047029, d is substantially 0.091067, e is substantially 0.00074, and f is substantially 24.18731.

* * * * *